United States Patent [19]

Chemburkar et al.

[11] Patent Number: 5,714,633
[45] Date of Patent: Feb. 3, 1998

[54] PROCESS FOR THE PREPARATION OF ARYLALKYNYL-N-HYDROXYUREA DERIVATIVES HAVING LIPOXYGENASE INHIBITORY ACTIVITY

[75] Inventors: Sanjay R. Chemburkar, Gurnee; Hemantkumar H. Patel, Waukegan; David P. Sawick, Wildwood; Albert V. Thomas, Vernon Hills, all of Ill.

[73] Assignee: Abbott Laboratories, Abbott Park, Ill.

[21] Appl. No.: 698,674

[22] Filed: Aug. 16, 1996

Related U.S. Application Data

[60] Provisional application No. 60/003,578, Sep. 12, 1995.
[51] Int. Cl.⁶ .................... C07C 275/04; C07C 275/18
[52] U.S. Cl. ............................................. 564/56; 564/52
[58] Field of Search ................................. 564/56, 52

[56] References Cited

U.S. PATENT DOCUMENTS

| | | | |
|---|---|---|---|
| 5,185,363 | 2/1993 | Brooks et al. | 514/438 |
| 5,288,751 | 2/1994 | Brooks et al. | 514/438 |
| 5,476,873 | 12/1995 | Brooks et al. | 514/595 |
| 5,559,144 | 9/1996 | Brooks et al. | 514/445 |

FOREIGN PATENT DOCUMENTS

| | | |
|---|---|---|
| 9201682 | 2/1992 | WIPO . |
| 9512589 | 5/1995 | WIPO . |

OTHER PUBLICATIONS

PCT International Search Report corresponding to PCT/US96/13892, 1996.

Lee et al.; J. Org. Chem. 1993 48, 24–31.

*Primary Examiner*—Shailendra Kumar
*Attorney, Agent, or Firm*—Frank Z. Yang

[57] ABSTRACT

The present invention provides a process for the preparation of a compound of formula

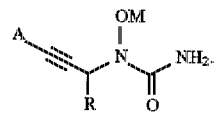

wherein R is a straight or branched alkyl group of from one to twelve carbon atoms; M represents hydrogen or a pharmaceutically acceptable cation; and A is selected from optionally substituted carbocyclic phenyl.

4 Claims, No Drawings

PROCESS FOR THE PREPARATION OF ARYLALKYNYL-N-HYDROXYUREA DERIVATIVES HAVING LIPOXYGENASE INHIBITORY ACTIVITY

This application claims benefit of Provisional application Ser. No. 60/003,598, filed Sept. 12, 1995.

TECHNICAL FIELD

This invention relates to a process useful for the synthesis of organic compounds. More particularly, this invention concerns a method of synthesis of arylalkynyl-N-hydroxyurea leukotriene biosynthesis inhibitors.

BACKGROUND OF THE INVENTION

Numerous studies have implicated leukotrienes as important mediators of asthma, allergy, arthritis, psoriasis, and inflammation. Arylalkynyl-N-hydroxyureas, as exemplified by N-hydroxy-N-[4-(3-(4-fluorophenoxy)phenyl)-3-butyn-2-ylurea are potent leukotriene biosynthesis inhibitors and are disclosed in U.S. Pat. No. 5,476,873 which is incorporated herein by reference. Blocking the formation of leukotrienes with agents such as N-hydroxy-N-[4-(3-(4-fluorophenoxy)phenyl)-3-butyn-2-ylurea offers treatment for leukotriene mediated afflictions in man and animals.

Several methods for incorporation of the N-hydroxyurea moiety have been employed (see, for example, U.S. Pat. No. 5,288,751). For example, the anion of an arylacetylene was reacted with the nitrone prepared from acetaldehyde and 5-hydroxypentanal oxime and the resulting adduct deprotected in situ and reacted with trimethysilylisocyanate to form the desired arylaklynyl-N-hydroxyurea. Alternatively, the arylacetylene anion was reacted with acetaldehyde, and the resulting alcohol coupled with a protected hydroxylamine derivative such as N,O-bis-t-butyloxycarbonylhydroxylamine or N,O-bis-phenyloxycarbonylhydroxylamine under Mitsunobu conditions (triphenylphosphine, diethyl- or diisopropylazodicarboxylate; see Lee, B. H., and Miller, M. J., J. Org. Chem., 1983, 48, 24–31 and references cited therein). Either deprotection of the Mitsunobu adduct followed by reaction with trimethylisocyanate, or aminolysis of the Mitsunobu adduct with ammonia or ammonium hydroxide provided the desired arylalkynyl-N-hydroxyurea.

Treatment of aryl halides with 3-butyn-2-ol in a palladium (II) catalyzed coupling reaction provided arylalkynol intermediates which were converted to the N-hydroxyurea derivatives by the Mitsunobu/aminolysis route described above. Alternatively, the alkynyl-N-hydroxyurea moiety was introduced in a Palladium (II) catalyzed coupling reaction between aryl halides and the desired N-hydroxy-N-alkynylurea, which was prepared in a separate, multistep sequence.

The preparations described above in which the aryl alkynyl derivative is prepared from the alkynol utilizing, the Mitsunobu reaction require expensive, custom-prepared hydroxylamine derivatives and generate solid waste byproducts which present disposal difficulties when conducted on a large scale. The Mitsunobu adduct must then be deprotected to prepare the final product.

SUMMARY OF THE INVENTION

The present invention provides a process for the preparation of a compound of formula wherein R is a straight or branched alkyl group of from one to twelve carbon atoms; M represents hydrogen or a pharmaceutically acceptable cation; and A is selected from the group consisting of (a) phenyl and; (b) phenyl substituted by one or more substituents selected from the group consisting of (1) alkyl of from one to six carbon atoms, (2) haloalkyl of from one to six carbon atoms, (3) alkoxy of from one to twelve carbon atoms, (4) hydroxy, (5) fluorine, (6) chlorine, (7) phenyl, (8) phenyl substituted with a substituent selected from the group consisting of (i) alkyl of from one to six carbon atoms, (ii) alkoxy of from one to six carbon atoms, (iii) fluorine, and (iv) chlorine; (9) phenoxy; (10) phenoxy optionally substituted with a substituent selected from the group consisting of (i) alkyl of from one to six carbon atoms, (ii) alkoxy of from one to six carbon atoms, (iii) fluorine, and (iv) chlorine, (11) phenylthio; and (12) phenylthio optionally substituted with a substituent selected from the group consisting of (i) alkyl of from one to six carbon atoms, (ii) alkoxy of from one to six carbon atoms, (iii) fluorine and, (iv) and chlorine.

The process comprises the steps of (1) coupling a compound of formula A—X, wherein A is defined above and X is selected from the group consisting of iodine, bromine, methanesulfonyl, or trifluoro-methanesulfonyl with a compound of formula

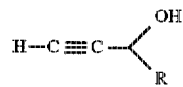

wherein R is defined above, to form a compound of formula

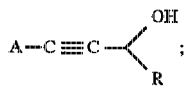

(2) converting the product of step 1 to a compound of formula

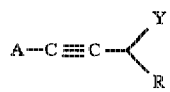

wherein Y is Br or Cl;

(3) reacting the product of step 2 with hydroxylamine to form a compound of formula

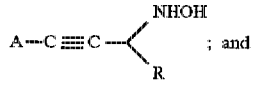

; and (4) reacting the product of step 3 with cyanate to formula

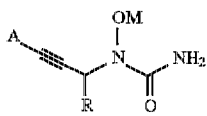

DETAILED DESCRIPTION OF THE INVENTION DEFINITIONS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkynyl" refers to a divalent group derived by the removal of two hydrogen atoms from a straight or branched chain acyclic hydrocarbon group containing a carbon-carbon triple bond.

The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl and the like.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts, and the like. (See, for example S. M. Berge, et al., *Pharmaceutical Salts*, J. Pharm. Sci., 1977, 66: 1–19).

PREFERRED EMBODIMENTS

In a preferred embodiment, step 3 above comprises displacement of Cl or Br with aqueous hydroxylamine.

In a particularly preferred embodiment, A is phenoxyphenyl, optionally substituted with alkyl of one to six carbon atoms, alkoxy of from one to twelve carbon atoms, chlorine, or fluorine.

In the most preferred embodiment, the process of the present invention is employed for the production of N-hydroxy-N-[4-(3-(4-fluorophenoxy)-phenyl)-3-butyn-2-yl]urea by carrying out the seeps of
(1) coupling 3-(4-fluorophenoxy)iodobenzene with 3-butyn-2-ol to form 4-[3-(4-fluorophenoxy)phenyl]-3-butyn-2-ol;

(2) converting the product of step 1 to 2-bromo-4-[3-(4-fluoro-phenoxy)phenyl]-3-butyne;

(3) reacting the product of step 2 with aqueous hydroxylamine to form N-[4-(3-(4-fluorophenoxy)phenyl)-3-butyn-2-yl]hydroxylamine; and (4) reacting the product of step 3 with cyanate to produce N-hydroxy-N-[4-(3-(4-fluorophenoxy)phenyl)-3-butyn-2-yl]urea.

The process of the invention is illustrated in Scheme 1. Arylalkynol $\underline{2}$ is prepared by the palladium-catalyzed coupling of A–X, (where A is defined above and X is Br, I, methanesulfonyl, or trifluoro-methanesulfonyl, preferably I), and alkynol $\underline{1}$ in the presence of tri-phenylphosphine, CuI, and base (for example diethylamine, triethyl-amine, diisopropylamine and the like, preferably diisopropylamine). Suitable palladium (II) catalysts include $Pd(OAc)_2$, $Pd(Ph_3P)_2Cl_2$, $Pd(CH_3CN)_2Cl_2$, preferably $Pd(CH_3CN)_2Cl_2$. Representative solvents for the coupling reaction include acetonitrile, ethyl acetate, toluene, tetrahydrofuran, aqueous tetrahydrofuran, ether, methyl-tert-butylether and the like, preferably methyl-tert-butyl ether. The reaction temperature is preferably 0°–10° C. Arylalkynol $\underline{2}$ is then converted to haloarylalkyne $\underline{3}$ (Y is Br or Cl), by reaction with chlorotrimethyl-silane/LiBr, $P(OPh)_3 \cdot Br_2$, or preferably $PBr_3$ (Y=Br), or p-toluenesulfonyl chloride/base (Y=Cl). Displacement of Y to form arylalkynyl-hydroxylamine $\underline{4}$ is accomplished by treatment of a solution of $\underline{3}$ in an alcoholic or dipolar aprotic organic solvent (for example methanol, ethanol, isopropanol, dimethylformamide, N-methyl-2-pyrrollidinone, and the like, preferably ethanol or N-methyl-2-pyrrollidinone), with aqueous hydroxylamine. The reaction in ethanol requires elevated temperatures to achieve an acceptable rate, but proceeds at ambient temperature in N-methyl-2-pyrrollidinone. Reaction of $\underline{4}$ with cyanate ion, preferably KOCN, provides arylalkynyl-N-hydroxyurea $\underline{5}$. The reaction is preferably conducted in an organic solvent such as ethyl acetate at a temperature around 0° C.

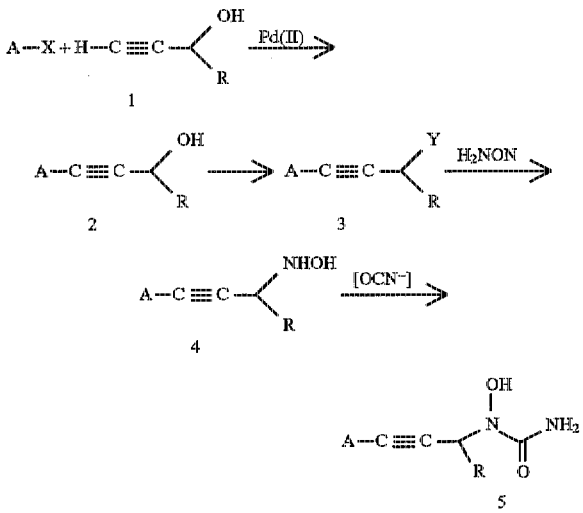

The foregoing may be better understood by the following Example, which is presented for purposes of illustration and is not intended to limit the scope of the inventive concept. The following reaction sequence was carried out in a single reaction vessel with no isolation or purification of intermediates.

Preparation of N-hydroxy-N-[4-(3-(4-fluorophenoxy)phenyl)-3-butyn-2-yl]urea

Step 1: 4-[3-(4-fluorophenoxy)phenyl]-3-butyn-2-ol

A 30-gallon, glass-lined reactor was charged with 3-(4-fluoro-phenoxy)-iodobenzene (10.0 kg), copper(I) iodide (60.6 g), triphenyl-phosphine (95.0 g), bis(acetonitrile) palladium(II) chloride, and methyl t-butyl ether (27 kg). The mixture was cooled to 0°–10° C. and 55% aqueous 3-butyn-2-ol (4.20 kg) was added. Diisopropylamine (3.8 kg) was added to initiate the reaction and N$_2$ was bubbled up from the bottom valve for a few minutes to agitate the reaction mixture. The reaction mixture was agitated at 15°–25° C. for 1.5 hours and then quenched by addition of 28% aqueous ammonia (12 kg) and brine (30 kg). The layers were separated and the organic phase was washed sequentially with brine (35 kg), 10% aqueous HCl (18 kg), 10% aqueous NaHCO$_3$ (18 kg), and brine (35 kg). The organic phase was then stirred for 45 minutes with anhydrous MgSO$_4$ (1.5 kg), PWA carbon (1.0 kg), and Ultra Norit C (1.0 kg) and filtered to give a solution of 4-[3-(4-fluorophenoxy)phenyl]-3-butyn-2-ol in methyl t-butyl ether which was used in the next step.

Step 2: 2-bromo4-[3-(4-fluorophenoxy)phenyl]-3-butyne

The solution of 4-[3-(4-fluorophenoxy)phenyl]-3-butyn-2-ol in methyl t-butyl ether prepared in step 1 was cooled to 0°–10° C. and PBr$_3$ (7.6 kg) was added slowly to maintain the reaction temperature under 15° C. The reaction mixture was agitated for 2 hours and then was quenched by the addition of chilled distilled water (25 kg). The layers were separated and the organic phase was diluted with methyl t-butyl ether, washed with distilled water and 5% aqueous NaHCO$_3$, and concentrated in vacuo to give 2-bromo-4-[3-(4-fluorophenoxy)phenyl]-3-butyne.

Step 3: N-[4-(3-(4-fluorophenoxy)phenyl)-3-butyn-2-yl] hydroxylamine

The 2-bromo-4-[3-(4-fluorophenoxy)phenyl]-3-butyne prepared in step 2 was taken up in N-methyl-2-pyrollidinone (27 kg) and 50% aqueous hydroxylamine (21 kg) was added. The reaction mixture was agitated for 2.5 hours at ambient temperature and then was diluted with distilled water (18 kg). The layers were separated and the organic phase was concentrated in vacuo to give N-[4-(3-(4-fluorophenoxy)phenyl)-3-butyn-2-yl]hydroxylamine.

Step 4: N-hydroxy-N-[4-(3-(4-fluorophenoxy)phenyl)-3-butyn-2-yl]urea

The N-[4-(3-(4-fluorophenoxy)phenyl)-3-butyn-2-yl] hydroxylamine prepared in step 3 above was taken up in ethyl acetate (36 kg) and cooled to 5° C. A solution of freshly prepared potassium isocyanate (10 kg) in water (18 kg) was slowly added and the exotherimic reaction was maintained below 10° C. The reaction mixture was agitated for 30 min. The layers were separated and the organic phase was dried over MgSO$_4$ and filtered. The filtrate was diluted with heptane (58 kg) and agitated for one hour. The resulting crude product was filtered, dissolved in 45° C. ethyl acetate (42 kg). PWA carbon (0.5 kg) and Ultra Norit C (0.5 kg) were added and the mixture was agitated for 30 minutes and filtered. The combined filtrate and washings were diluted with heptane (68 kg) and filtered to provide N-hydroxy-N-[4-(3-(4-fluorophenoxy)phenyl)-3-butyn-2-yl]urea (2.94 kg). m.p. 139°–40° C.; $^1$H NMR (d$_6$ Me$_2$SO) 1.33 (d, 3, J=7 Hz), 5.10 (q, 1, J=7 Hz), 6.55 (s, 2), 6.87 (m, 1), 7.03 (m, 1), 7.13 (m, 3), 7.25 (t, 2, J=8 Hz), 7.37 (t, 1, J=8 Hz), 9.33 (s, 1) ppm; mass spectrum m/e (rel intensity) 332 (80, M$^+$+NH$_4$), 315 (75, M$^+$+H), 289 (80), 272 (100). Analysis calculated for C$_{17}$H$_{15}$FN$_2$O$_3$: C, 64.95, H, 4.81, N, 8.91; found: C, 64.67, H, 4.76, N, 8.81.

We claim:

1. A process for the preparation of a compound of formula

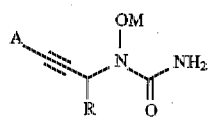

wherein R is a straight or branched alkyl group of from one to twelve carbon atoms;

M represents hydrogen, or a pharmaceutically acceptable cation;

A is selected from the group consisting of
(a) phenyl and
(b) phenyl substituted by one or more substituents selected from the group consisting of
  (1) alkyl of from one to six carbon atoms;
  (2) haloalkyl of from one to six carbon atoms;
  (3) alkoxy of from one to twelve carbon atoms;
  (4) hydroxy;
  (5) fluorine;
  (6) chlorine;
  (7) phenyl;
  (8) phenyl substituted with a substituent selected from the group consisting of
    (i) alkyl of from one to six carbon atoms;
    (ii) alkoxy of from one to six carbon atoms;
    (iii) fluorine; and
    (iv) chlorine;
  (9) phenoxy;
  (10) phenoxy substituted with a substituent selected from the group consisting of
    (i) alkyl of from one to six carbon atoms;
    (ii) alkoxy of from one to six carbon atoms;
    (iii) fluorine; and
    (iv) chlorine;
  (11) phenylthio;
  (12) phenylthio substituted with a substituent selected from the group consisting of
    (i) alkyl of from one to six carbon atoms;
    (ii) alkoxy of from one to six carbon atoms;
    (iii) fluorine; and
    (iv) chlorine;

the process comprising the steps of:

(1) coupling a compound of formula A—X, wherein A is defined above and X is selected from the group consisting of iodine, bromine, methanesulfonyl, and trifluoromethanesulfonyl with a compound of formula

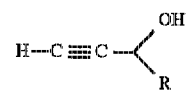

wherein R is defined above, to form a compound of formula

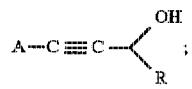

(2) converting the product of step 1 to a compound of formula

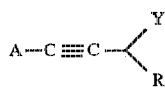

R wherein Y is Br or Cl;

(3) reacting the product of step 2 with hydroxylamine to form a compound of formula

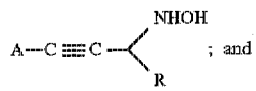

; and (4) reacting the product of step 3 with cyanate to form

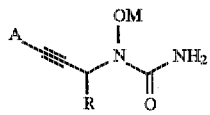

2. The process of claim 1, wherein said step 3 involves reaction of a compound of formula

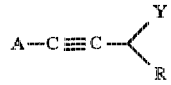

wherein Y is Br or Cl with aqueous hydroxyamine to form a compound of formula

A—C≡C—C(NHOH)(R)

3. The process of claim 2, wherein A is selected from the group consisting of phenoxyphenyl, and phenoxyphenyl optionally substituted with a substituent selected from the group consisting of alkyl of one to six carbon atoms, alkoxy of from one to twelve carbon atoms, fluorine, and chlorine.

4. The process of claim 3, which comprises:

(1) coupling of 3-(4-fluorophenoxy)iodobenzene with 3-butyn-2-ol to form 4-[3-(4-fluorophenoxy)phenyl]-3-butyn-2-ol;

(2) conversion of the product of step 1 to 2-bromo-4-[3-(4-fluorophenoxy)phenyl]-3-butyne;

(3) reaction of the product of step 2 with aqueous hydroxylamine to form N-[4-(3-(4-fluorophenoxy)phenyl)-3-butyn-2-yl]hydroxylamine; and (4) reaction of the product of step 3 is with cyanate to produce N-hydroxy-N-[4-(3-(4-fluorophenoxy)phenyl)-3-butyn-2-yl]urea.

* * * * *